United States Patent
Wang

(10) Patent No.: US 7,190,460 B2
(45) Date of Patent: Mar. 13, 2007

(54) FOCUSING OPTICS FOR SMALL SPOT OPTICAL METROLOGY

(75) Inventor: David Y. Wang, Fremont, CA (US)

(73) Assignee: Therma-Wave, Inc., Fremont, CA (US)

(*) Notice: Subject to any disclaimer, the term of this patent is extended or adjusted under 35 U.S.C. 154(b) by 437 days.

(21) Appl. No.: 10/695,007

(22) Filed: Oct. 28, 2003

(65) Prior Publication Data
US 2004/0125369 A1   Jul. 1, 2004

Related U.S. Application Data

(60) Provisional application No. 60/429,152, filed on Nov. 26, 2002.

(51) Int. Cl.
*G01N 21/47* (2006.01)

(52) U.S. Cl. ................... 356/446; 356/237.5

(58) Field of Classification Search ........ 356/445–448, 356/237.2–237.5; 359/859
See application file for complete search history.

(56) References Cited

U.S. PATENT DOCUMENTS

| | | | | |
|---|---|---|---|---|
| 3,524,983 A * | 8/1970 | Voelz | ...................... | 356/448 |
| 4,205,902 A * | 6/1980 | Shafer | ....................... | 359/859 |
| RE32,912 E * | 4/1989 | Doyle | ....................... | 356/244 |
| 5,106,196 A * | 4/1992 | Brierley | ...................... | 356/445 |
| 5,608,526 A | 3/1997 | Piwonka-Corle et al. | ... | 356/369 |
| 5,661,561 A * | 8/1997 | Wurz et al. | .................. | 356/635 |
| 5,917,594 A | 6/1999 | Norton | ....................... | 356/327 |
| 6,310,687 B1 * | 10/2001 | Stumbo et al. | ............. | 356/317 |
| 6,778,273 B2 * | 8/2004 | Norton et al. | ............... | 356/445 |

* cited by examiner

*Primary Examiner*—Richard A. Rosenberger
(74) *Attorney, Agent, or Firm*—Stallman & Pollock LLP

(57) ABSTRACT

A system for focusing broadband light within a reflectometer includes a concave spherical mirror for gathering light from the surface of a sample under inspection. The concave spherical mirror projects the received light to a convex spherical mirror. The combination of the two mirrors captures the light diverging from the sample and collimates the light into parallel rays. The light can then be passed through an aperture prior to entering a detector. Each of the two mirrors is fabricated as an off-axis section of a spherical mirror and positioned to form a partial Schwarzschild design without the associated problem of a central obscuration.

4 Claims, 6 Drawing Sheets

FOCUSING OPTICS FOR SMALL SPOT OPTICAL METROLOGY

PRIORITY CLAIM

The present application claims priority to U.S. Provisional Patent Application Ser. No. 60/429,152, filed Nov. 26, 2002, which is incorporated herein by reference

TECHNICAL FIELD

This invention relates to optical tools for measuring and evaluating semiconductor wafers. In particular, the present invention relates to objectives used to focus light onto semiconductor wafers and to gather light reflected by semiconductor wafers as part of a measurement process.

BACKGROUND OF THE INVENTION

As semiconductor geometries continue to shrink, manufacturers have increasingly turned to optical techniques to perform non-destructive inspection and analysis of semiconductor wafers. Techniques of this type, known generally as optical metrology, operate by illuminating a sample with an incident field (typically referred to as a probe beam) and then detecting and analyzing the reflected energy. Ellipsometry and reflectometry are two examples of commonly used optical techniques. For the specific case of ellipsometry, changes in the polarization state of the probe beam are analyzed. Reflectometry is similar, except that changes in intensity are analyzed. Scatterometry is a specific type of optical metrology that is used when the structural geometry of a sample creates diffraction (optical scattering) of the probe beam. Scatterometry systems analyze diffraction to deduce details of the structures that cause the diffraction to occur.

Various optical techniques have been used to perform optical scatterometry. These include broadband spectroscopy (U.S. Pat. Nos. 5,607,800; 5,867,276 and 5,963,329), spectral ellipsometry (U.S. Pat. No. 5,739,909) single-wavelength optical scattering (U.S. Pat. No. 5,889,593), and spectral and single-wavelength beam profile reflectance and beam profile ellipsometry (U.S. Pat. No. 6,429,943). Scatterometry, in these cases generally refers to optical response information in the form of diffraction orders produced by periodic structures (e.g., gratings on a wafer). In addition it may be possible to employ any of these measurement technologies, e.g., single-wavelength laser BPR or BPE, to obtain critical dimension (CD) measurements on non periodic structures, such as isolated lines or isolated vias and mesas. The above cited patents and patent applications, along with PCT Application WO03/009063, US Application 2002/0158193, US Application 2003/0147086, US Application 2001/0051856 A1, PCT Application WO 01/55669 and PCT Application WO 01/97280 are all incorporated herein by reference.

As shown in FIG. 1, a typical optical metrology system includes an illumination source that creates a monochromatic or polychromatic probe beam. The probe beam is projected by one or more lenses onto the surface of a sample. The portion of the sample surface that is illuminated by the probe beam is referred to as the illumination spot. The sample reflects the probe beam and the reflected probe beam (or a portion of the reflected probe beam) is transported to a detector. For most systems, the detector gathers energy from a small area within the sample surface known as the measurement spot. The measurement spot may be smaller or larger than the illumination spot. The detector transforms the energy it receives into corresponding output signals. A processor analyzes the signals to measure the structure or composition of the sample. For cases where the probe beam is polychromatic, the detector is often preceded by an optical element that disperses the incoming probe beam into different wavelengths. A prism or grating may be used for this purpose. This allows different portions of the detector to measure different spectral components of the reflected probe beam off the sample. In these cases, the combination of the spreading optical component and the detector is generally referred to as a spectrometer.

The decreasing size of semiconductor geometries forces metrology to analyze increasingly small areas. In practice, the area being measured is typically a test feature that is often less than 50 μm wide and is often surrounded by a completely different material or film stack. Accurately analyzing small areas requires that the illumination spot and the measurement spot be relatively small. This, in turn requires that the incoming and reflected probe beams be tightly focused to support small spot sizes.

One way of meeting these requirements (at least partially) is by using small angles of incidence for the incoming and reflected probe beams. Small angle of incidence systems reduce the amount by which the sample projects the illumination and measurement spots. This is one of the main motivations behind metrology systems of the type shown in FIG. 2 in which the incoming and reflected probe beams are directed normally to the sample surface. As may be appreciated, the use of normal incidences means that the illumination and measurement spots have a circular cross-section. The circular cross-section is effectively smaller than the elliptical cross-section associated with non-normally directed beams.

In systems where normal incidence is used (e.g., the system of FIG. 2) the focusing assembly transports both the incident and the reflected probe beam. This differs from non-normal systems where distinct optical components are used for incident and reflected probe beams. Several focusing assemblies have been developed for this purpose. These focusing assemblies can be formed from refractive or reflective elements or a combination of refractive and reflective elements. Of the different designs, refractive designs are attractive because they have no central and peripheral [e.g., spider arms] obscurations that may cause scattering within the metrology tool. Unfortunately, chromatic aberrations are inherent in refractive optics. Minimizing such aberration over the wavelength range of DUV to IR is difficult while maintaining small spot sizes.

It is another common practice to use rotationally symmetric reflective designs such as Schwarzschild microscope objectives. As shown in FIG. 3, a classical Schwarzschild objective consists of a large primary concave and a small secondary convex mirror system in which the two mirrors are or nearly monocentric. The two mirrors form a path between an illumination source or a detector (or both) and the surface of a sample. Unfortunately, the secondary mirror forms a central obscuration and secondary mirror hardware support structures form spider arm obscurations. The central obscuration blocks useful probe beam at and near zero numerical aperture and increases diffraction effects. Further, the spider arm obscurations introduce scatters as a function of spider arms geometry which is undesirable when measuring patterned structures.

SUMMARY OF THE INVENTION

The present invention includes a system for focusing broadband light within an ellipsometer, reflectometer or other optical metrology tool. One implementation of the focusing system uses a two-mirror system. A concave spherical mirror is used to gather light from the surface of a sample under inspection. The concave spherical mirror projects the received light to a convex spherical mirror. The combination of the two mirrors captures the light diverging from the sample and collimates the light into parallel rays. The light can then be passed through an aperture stop prior to entering a detector.

Each of the mirrors is an off-axis section of a parent spherical mirror. The two parent mirrors are monocentric or nearly monocentric (i.e., they have the same or nearly the same center of curvatures). The aperture stop is located at or near one of the mirrors, (i.e. pupil-centric design). This design utilizes the beneficial monocentric and pupil-centric properties of the parent mirrors and can be substantially free of third order spherical aberration, coma and astigmatism and chromatic aberration. The mirror radii are chosen for small focal spot. The mirror offsets and spacing are chosen to avoid beam obscuration. Additional optics may be added to the base design to achieve telecentricity or improve spot size or achieve desired probe beam incidence angle at the sample. This design obtains many of the benefits of a conventional Schwarzschild design without the associated diffraction effects of a central obscuration.

A second implementation of the focusing system replaces the convex spherical mirror with a flat mirror. The concave spherical mirror is replaced with an off axis paraboloid mirror. In either implementation, the focusing system may be placed on the illumination side or collection side of a reflectometer or other optical metrology tool.

DETAILED DESCRIPTION OF THE PREFERRED EMBODIMENTS

Figure 1:
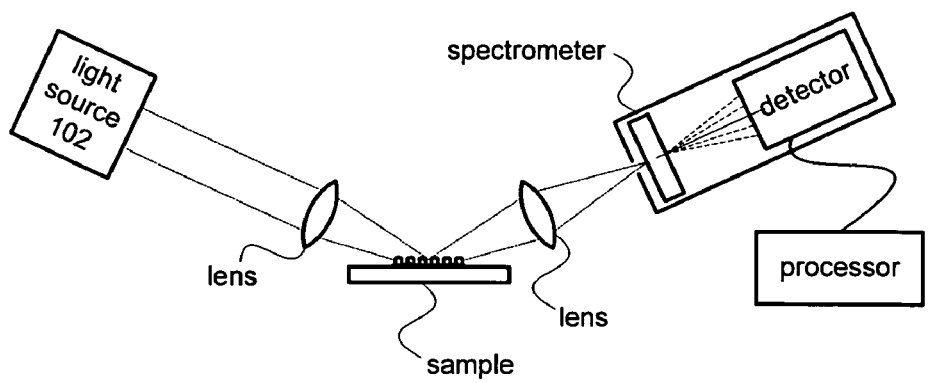
FIG. 1 is a block diagram of a prior art optical metrology system.
Figure 2:
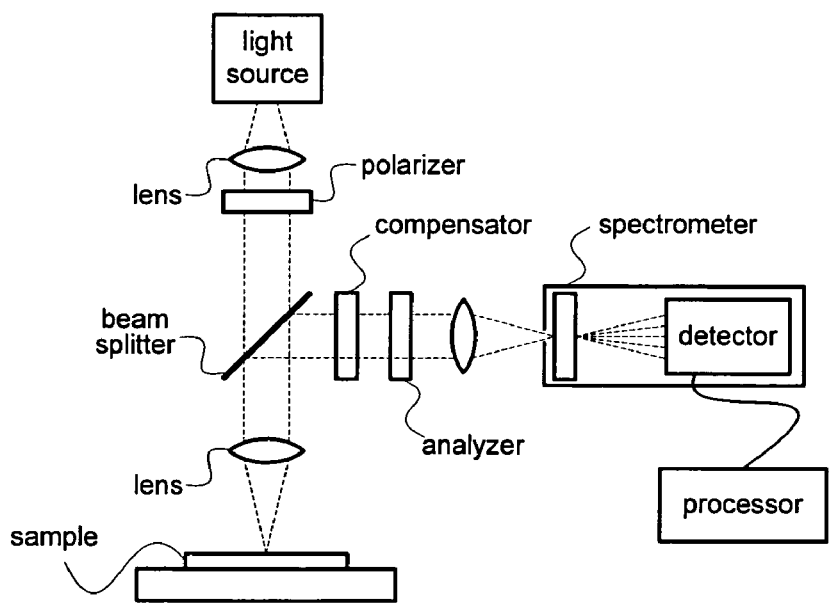
FIG. 2 is a block diagram of a prior art optical metrology system in which the incident and reflected beams are normally directed with respect to the sample.
Figure 3:
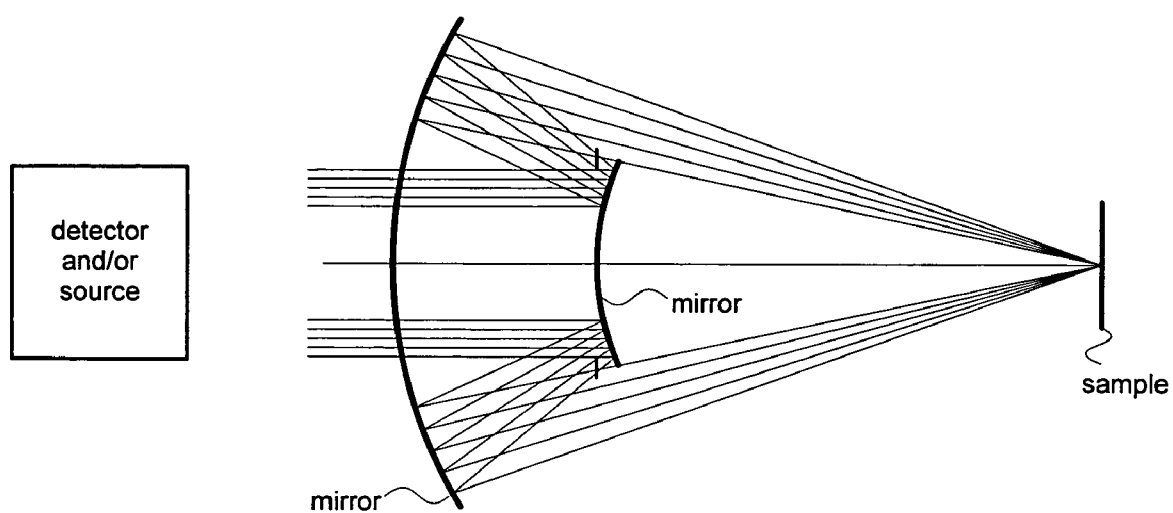
FIG. 3 shows a prior art Schwarzschild microscope objective.
Figure 4A:
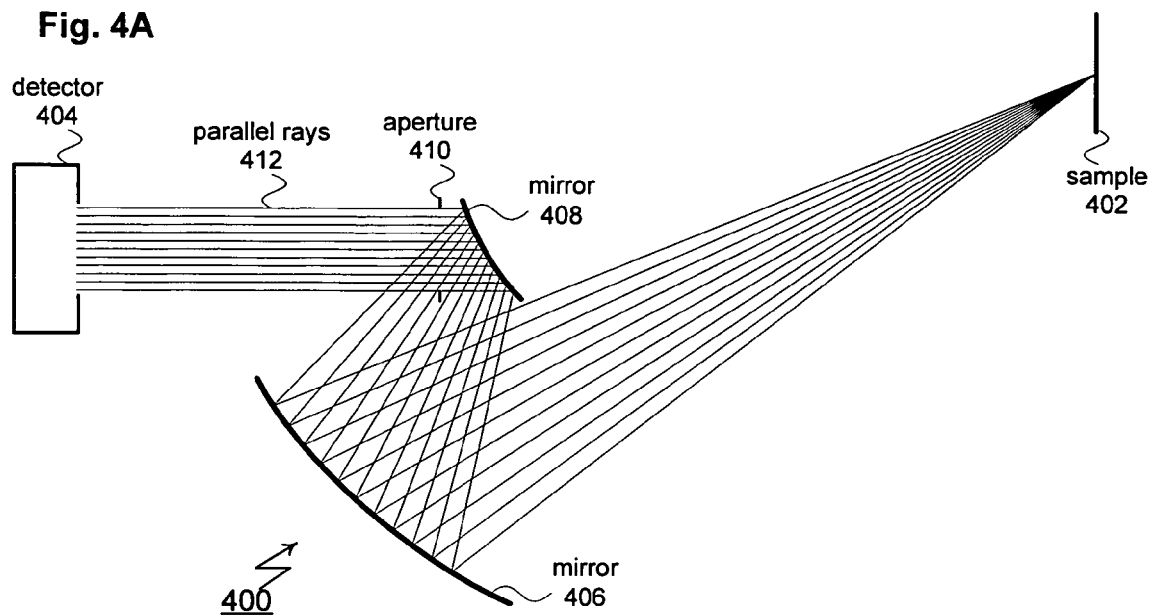
FIG. 4A shows a first implementation of a focusing system as provided by the present invention.
Figure 4B:
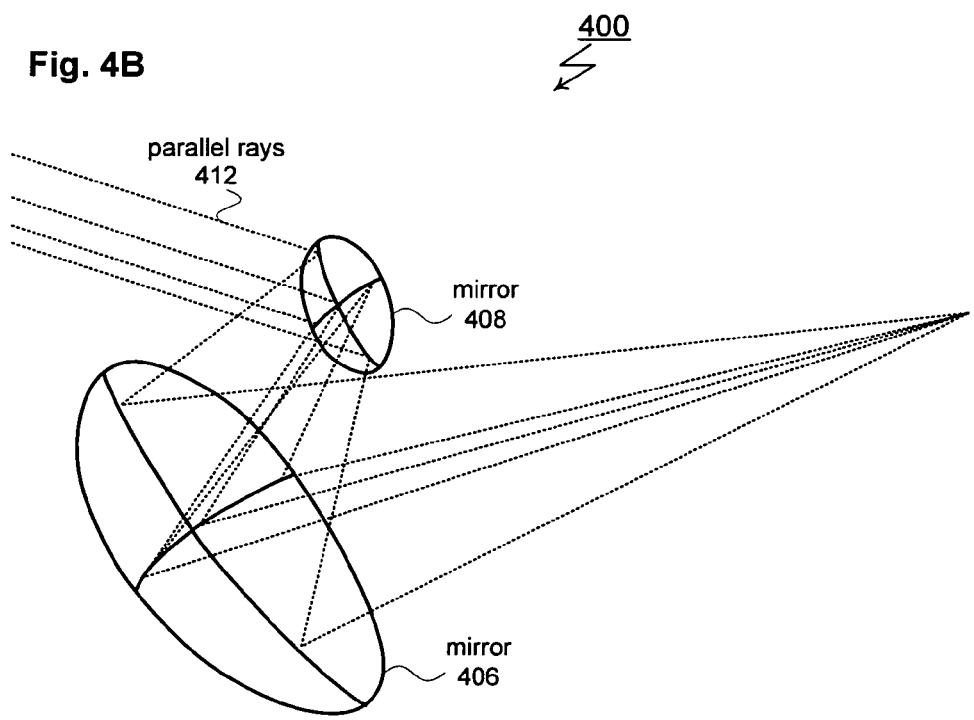
FIG. 4B is a perspective view of the focusing system of FIG. 4A.

The present invention includes a system for focusing broadband light within an ellipsometer, reflectometer or other optical metrology tool. One possible implementation for the focusing system is shown in FIGS. 4A and 4B with the general designation 400. For this particular example, focusing system 400 is used on the collection side of an ellipsometer or reflectometer and is used to transport light from a sample 402 to a detector 404. Focusing system 400 may also be used on the illumination side of a metrology system to transport light from an illumination source to the surface of sample 402.

As shown in FIG. 4A, light reflected by sample 402 is collected by a concave spherical mirror 406. Spherical mirror 406 projects the received light to a convex spherical mirror 408. The combination of the two mirrors 406, 408 captures the light diverging from sample 402 and collimates the light into parallel rays 412. The light can then be passed through an aperture stop 410 prior to entering detector 404. Rays 412 are parallel specifically to support the case where focusing system 400 is used within a system (such as an ellipsometer) that includes a rotating compensator. For other systems, it is possible to fabricate mirrors 406, 408 so that rays 412 are not parallel.

Each of mirrors 406, 408 is an off-axis section of a parent spherical mirror. Mirrors 406, 408 are positioned as if their parents were monocentric or nearly monocentric (i.e., they have the same or nearly the same center of curvatures). Aperture stop 410 is located at or near one of the mirrors 406, 408 (i.e. pupil-centric design). This design utilizes the beneficial monocentric and pupil-centric properties of the parent mirrors and can be substantially free of third order spherical aberration, coma and astigmatism and chromatic aberration. The mirror radii are chosen for small focal spot. The mirror offsets and spacing are chosen to avoid beam obscuration. Additional optics may be added to the base design to achieve telecentricity or improve spot size. This design obtains many of the benefits of a conventional Schwarzschild design without the associated problem of a central obscuration.

Focusing system 400 has the following characteristics:

1. Small axial focal spot (<<50 um).
2. No chromatic aberration.
3. Significantly reduced spherical aberration (system is monocentric or near monocentric).
4. Significantly reduced coma or astigmatism (system is or near pupil centric).
5. No central obscuration.
6. Spherical mirror surfaces can be classically polished to a low surface roughness.
7. Mirror surfaces have low scatter since no diamond turning artifacts.
8. Angle of incidence range is +/−90 degrees.

The following table outlines one possible recipe for focusing system 400:

| Surface | Radius | Thickness | Y-decenter | Notes |
|---|---|---|---|---|
| Object | Infinity | Infinity | | Parallel ray 412 |
| 1 | Infinity | 0 | | |
| 2 | Infinity | 0 | | |
| 3 | Infinity | 32.51 | | |
| Stop | Infinity | 0 | | Aperture stop 410 |
| 5 | Infinity | 0 | 22 | Displacement from parent of 408 |
| 6 | 43.296 | −32.51 | | Reflective mirror 408 |
| 7 | 73.129 | 32.51 | | Reflective mirror 406 |
| 8 | Infinity | 80.08 | | |

-continued

| Surface | Radius | Thickness | Y-decenter | Notes |
|---|---|---|---|---|
| Image | Infinity | 0 | | Sample 402 |
| Effective Focal Length = 45.0 | | | | |
| F/Number = 4.5 | | | | |

Figure 5:
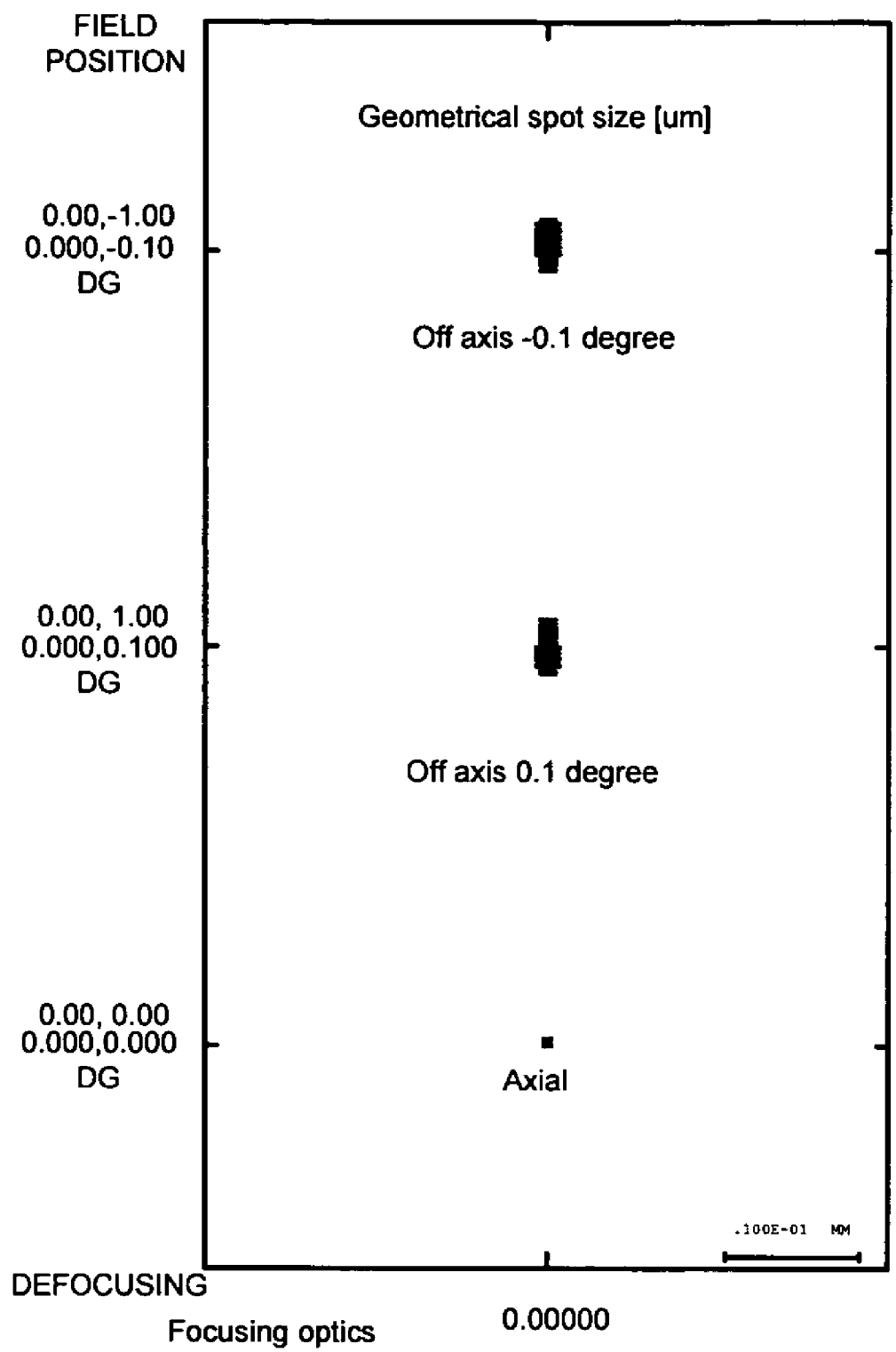
FIG. 5 is a computer generated plot showing the illumination or measurement spots and field height generated by the focusing system of FIG. 4.

FIG. 5 shows the spots sizes and field heights that can be achieved using the recipe in the preceding table. As shown in the lowermost portion of that figure, the axial spot size is substantially less than 50 µm. This spot size is achieved over the wavelength range of 190 nm to 900 nm. The middle and upper portions show the spot sizes at +0.1 degrees and −0.1 degrees, respectively.

As mentioned previously, focusing system 400 can be used for either collection or illumination. It is also possible to use focusing system 400 to provide both collection and illumination to the sample. This is accomplished by rotating focusing system 400 with respect to sample 402, so the incident and reflected probe beams have substantially normal incidence angle at sample 402. One or more flat mirrors may be added to focusing system 400, typically before mirror 406 or after mirror 408, so rays 412 and beam reflected off sample 402 are parallel, for purpose of packaging. A beam splitter is then used to is then used to simultaneously direct the probe beam output of an illumination source to mirror 408 (and on to sample 402) while allowing the returning probe beam to enter detector 404.

Figure 6A:
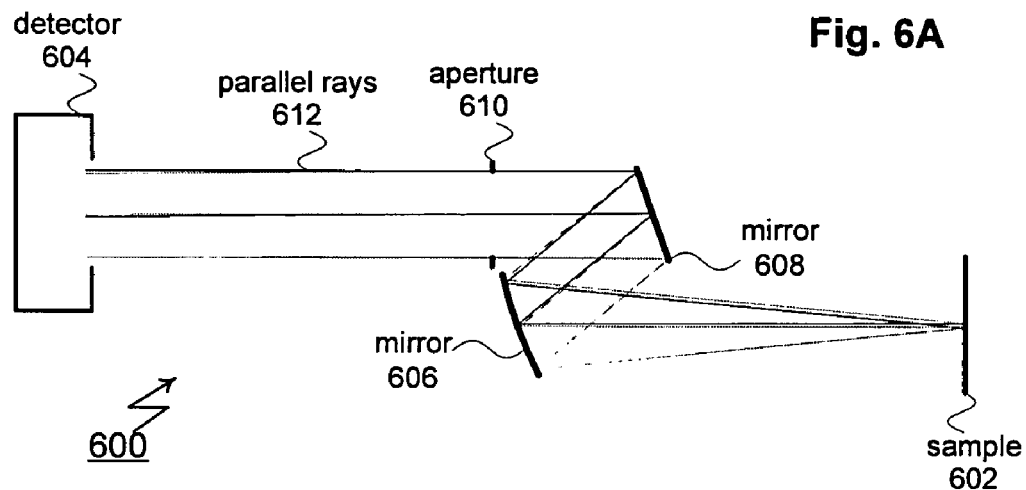
FIG. 6A shows a second implementation of a focusing system as provided by the present invention.
Figure 6B:
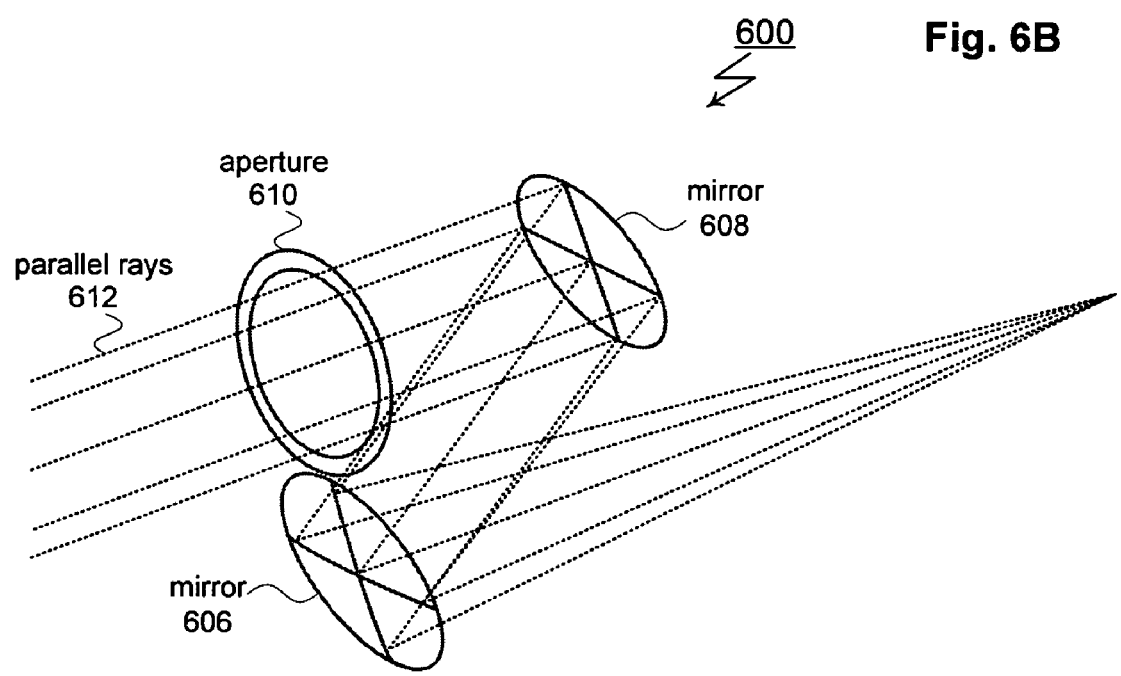
FIG. 6B is a perspective view of the focusing system of FIG. 6A.

A second possible implementation for the focusing system is shown in FIGS. 6A and 6B with the general designation 600. For this particular example, focusing system 600 is used on the collection side of an ellipsometer or reflectometer and is used to transport light from a sample 602 to a detector 604. Focusing system 600 may also be used on the illumination side of a metrology system to transport light from an illumination source to the surface of sample 602. In either case, the angle of incidence (or reflection) is substantially normal. This is the typical mode of operation to support normal incidence reflectometry, although it is also possible to use the illumination system 600 in non-normal applications.

As shown in FIG. 6A, light reflected by sample 602 is collected by a concave off-axis paraboloid mirror 606. Paraboloid mirror 606 collimates the received light and projects the received light to a flat mirror 608. Mirror 608 redirects the light to be substantially parallel to the reflected probe beam at sample 602. The combination of the two mirrors 606, 608 captures the light diverging from sample 602 and collimates the light into parallel rays 612. The light can then be passed through an aperture stop 610 prior to entering detector 604. Rays 612 are parallel specifically to support the case where focusing system 600 is used within a system (such as an ellipsometer) that includes a rotating compensator. For other systems, it is possible to fabricate mirrors 606, 608 so that rays 612 are not parallel. It is also possible to replace paraboloid mirror 606 with an ellipsoidal, toriodal or generalized aspheric mirror, to achieve small focus spot with non-collimated rays 612.

Focusing system 600 has the following characteristics:
1. Small axial focal spot (<<50 µm).
2. No chromatic aberration.
3. Significantly reduced spherical aberration.
4. No central obscuration.
5. Telecentric pupil.
6. Angle of incidence range is +/−90 degrees.

The following table outlines one possible recipe for focusing system 600:

| Surface | Radius | Thickness | Conic | Alpha tilt | Y-decenter | Notes |
|---|---|---|---|---|---|---|
| Object | Infinity | Infinity | | | | Parallel ray 612 |
| 1 | Infinity | 30 | | | | |
| Stop | Infinity | 15 | | | | Aperture stop 610 |
| 3 | Infinity | −21 | | 20 | | Reflective mirror 608 |
| 4 | Infinity | 0 | | | −26.2 | |
| 5 | 72 | 36 | −1 | | | Reflective mirror 606 |
| 6 | Infinity | 0 | | −40 | | |
| 7 | Infinity | 0 | | | | |
| Image | Infinity | 0 | | | | Sample 602 |
| Effective focal length = 36.0 | | | | | | |
| F/Number = 4.5 | | | | | | |

Figure 7:
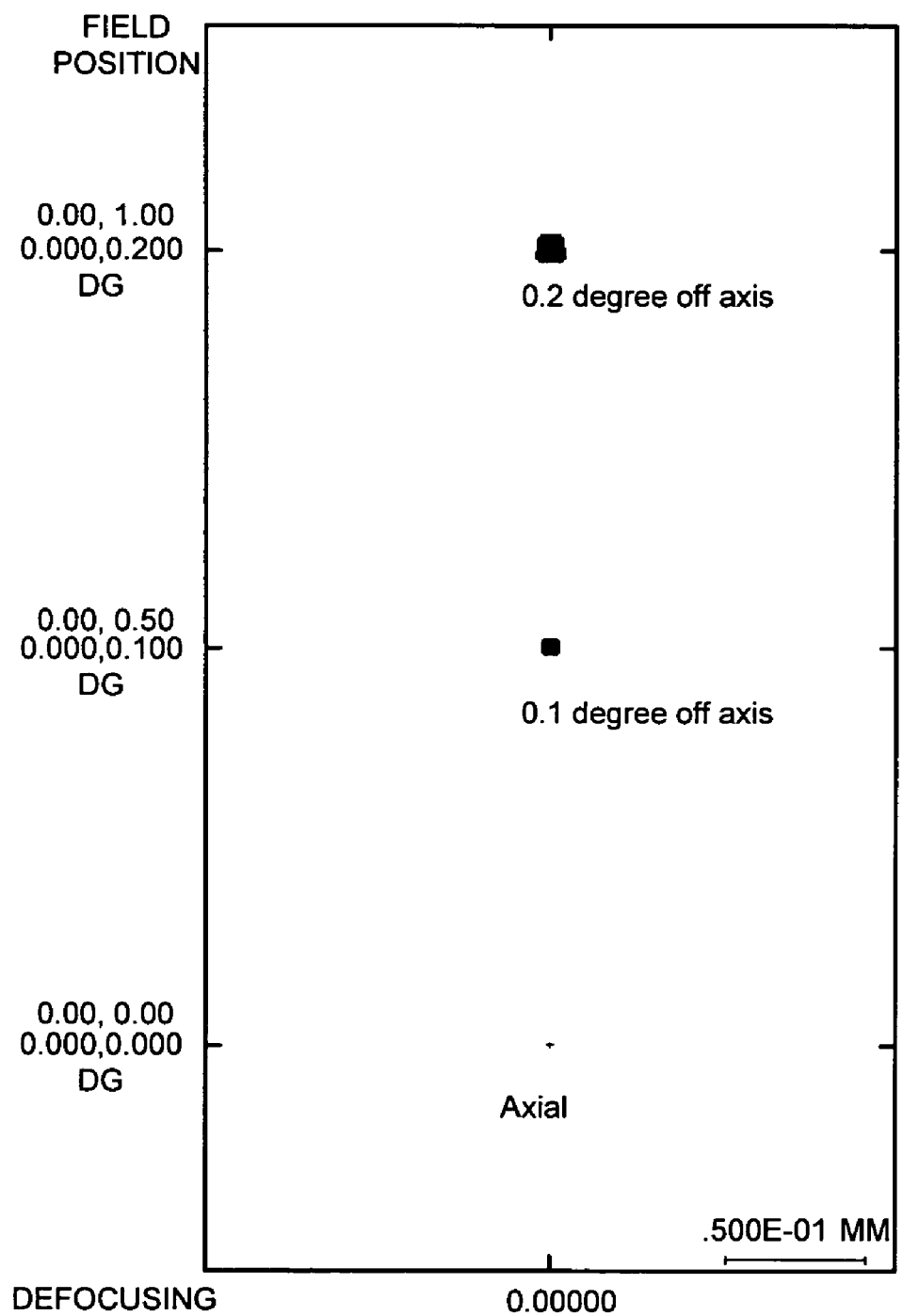
FIG. 7 is a computer generated plot showing the illumination or measurement spots and field height generated by the focusing system of FIG. 6.

FIG. 7 shows the spots sizes and field heights that can be achieved using the recipe in the preceding table. As shown in the lowermost portion of that figure, the axial spot size is substantially less than 50 µm. This spot size is achieved over the wavelength range of 190 nm to 900 nm. The middle and upper portions show the spot sizes at +0.1 degrees and −0.1 degrees, respectively.

Aspheric Constants:

$$Z = \frac{CY^2}{\sqrt{(1 + (1 - (1 + K)(C^2)Y^2))}} + \text{higher order coefficients}$$

Z is surface sag, C is curvature, Y is semi-aperture and K is conic constant.

As mentioned previously, focusing system 600 can be used for either collection or illumination. It is also possible to use focusing system 600 to provide both collection and illumination to the sample. Typically, this is accomplished by adding a beam splitter (or other optical device) between mirror 608 and detector 604. The beam splitter (not shown) allows the probe beam output of an illumination source to be directed to mirror 608 (and on to sample 602) while simultaneously allowing the returning probe beam to enter detector 604.

The 45 degree off-axis paraboloid mirror 606 [with smaller NA and equivalently larger airy diameter] has much tighter encircled energy [total energy vs. distance from core] values than corresponding 20× objective. This is because of the central obscuration of typical 20× objective diffracts several percent of the light out of the core.

Focusing systems 400 and 600 can be scaled to any size or focal length and may be used in a range of metrology systems of which ellipsometers and reflectometers are only examples.

What is claimed is:

1. A system for optically inspecting and evaluating a sample, the system comprising:
   a concave spherical mirror positioned to collect light reflected from a measurement spot on the sample surface;
   a convex spherical mirror positioned to receive and collimate the light collected by the concave spherical mirror with the convex and concave spherical mirrors positioned to be mutually non-obscuring and wherein the concave spherical mirror is fabricated as an off-axis section of a first spherical mirror and the convex spherical mirror is fabricated as an off-axis section of a second spherical mirror with the concave and convex spherical mirrors positioned to be substantially monocentric; and
   an aperture stop located near one of the mirrors.

2. A system for optically inspecting and evaluating a sample, the system comprising:
   a concave spherical mirror positioned to project a probe beam onto the sample surface;
   a convex spherical mirror positioned to redirect the probe beam towards the concave spherical mirror, with the convex and concave spherical mirrors positioned to be mutually non-obscuring and wherein the concave spherical mirror is fabricated as an off-axis section of a first spherical mirror and the convex spherical mirror is fabricated as an off-axis section of a second spherical mirror with the concave and convex spherical mirrors positioned to be substantially monocentric; and
   an aperture stop located near one of the mirrors.

3. A system for optically inspecting and evaluating a sample, the system comprising:
   a concave off-axis paraboloid mirror positioned to collect and to collimate diverging light reflected from a measurement spot on the sample surface at a substantially normal angle of reflection;
   a flat mirror positioned to receive and redirect the light collected by the paraboloid mirror with the paraboloid and flat mirrors positioned to be mutually non-obscuring;
   a detector positioned to received light redirected by the flat mirror; and
   an aperture stop located between the flat mirror and the detector and near the flat mirror.

4. A system for optically inspecting and evaluating a sample, the system comprising:
   a concave off-axis paraboloid mirror positioned to focus a probe beam onto the sample surface with a substantially normal angle of incidence;
   a flat mirror positioned to redirect the probe beam towards the paraboloid mirror, with the paraboloid and flat mirrors positioned to be mutually non-obscuring; and
   an aperture stop located near to and in front of the flat mirror.

* * * * *